United States Patent [19]

Rybak

[11] Patent Number: 5,013,155
[45] Date of Patent: May 7, 1991

[54] PORTABLE SPECTROPHOTOMETRIC INSTRUMENT HAVING VIAL HOLDER AND LIGHT INTEGRATOR

[75] Inventor: Franklyn M. Rybak, Glen Arm, Md.

[73] Assignee: Chemetrics, Inc., Calverton, Va.

[21] Appl. No.: 413,375

[22] Filed: Sep. 27, 1989

Related U.S. Application Data

[63] Continuation of Ser. No. 412,453, Sep. 26, 1989, abandoned.

[51] Int. Cl.⁵ ............... G01N 21/31; G01N 21/51
[52] U.S. Cl. ................. 356/408; 250/228; 356/414; 356/434; 356/440; 356/236
[58] Field of Search ............ 250/228; 356/236, 408, 356/409, 414, 434, 436, 432, 440, 246

[56] References Cited

U.S. PATENT DOCUMENTS

| | | | |
|---|---|---|---|
| 2,391,076 | 12/1945 | Stevens | 356/409 |
| 3,137,758 | 6/1964 | Mason et al. | |
| 3,370,503 | 2/1968 | Keahl | |
| 3,586,441 | 6/1971 | Smith et al. | |
| 3,676,004 | 7/1972 | Prugger et al. | |
| 3,704,950 | 12/1972 | Rosencranz | |
| 3,733,137 | 5/1973 | Badessa | |
| 3,761,183 | 9/1972 | Yuasa et al. | |
| 3,887,281 | 6/1975 | Kurita et al. | |
| 3,902,812 | 9/1975 | Honkawa | |
| 3,910,701 | 10/1975 | Henderson et al. | 356/432 X |
| 4,004,150 | 1/1977 | Natelson | 356/434 X |
| 4,047,819 | 9/1977 | Goldberg | |
| 4,167,331 | 9/1979 | Nielsen | |
| 4,248,536 | 2/1981 | Hijikata | 356/416 |
| 4,297,579 | 10/1981 | Spaeth | 356/434 X |
| 4,332,469 | 6/1982 | Wendland | 356/222 |
| 4,432,642 | 2/1984 | Tolles | 356/246 |
| 4,498,782 | 2/1985 | Proctor et al. | 356/436 |
| 4,544,271 | 10/1985 | Yamamoto | 356/328 |
| 4,566,797 | 1/1986 | Kaffka et al. | 356/402 |
| 4,575,240 | 3/1986 | Hess et al. | 356/246 |
| 4,690,560 | 9/1987 | Coogan | 356/236 X |
| 4,781,456 | 11/1988 | Nogani | 356/51 |
| 4,797,000 | 1/1989 | Curtis | 356/436 |

FOREIGN PATENT DOCUMENTS

WO82/00361 2/1982 World Int. Prop. O. ......... 356/414

OTHER PUBLICATIONS

"Double-Beam Densitometer and Comparator", by Carpenter et al. Analytical Chemistry, vol. 25, No. 10, Oct. 1953, pp. 1473-1477.

Primary Examiner—Vincent P. McGraw
Attorney, Agent, or Firm—Berman, Aisenberg & Platt

[57] ABSTRACT

A portable hand held instrument is capable of making accurate colorimetric measurements in the field. The instrument has a body which houses the electronic circuitry and a door which allows a vial having a solution to be measured to be placed therein. The vial is illuminated lengthwise by a light beam of two wavelengths, one of which serves as a reference. The light emerging from the top of the vial is spatially integrated and directed to a detector. The detector measures the intensity of the transmitted light, and the electronic circuit determines the difference between the logarithms of the detected signals. This difference is multiplied by a constant to produce a signal representative of the concentration and is displayed. The resolution of the measurement is automatically increased when the processor senses that the signals are too small.

9 Claims, 3 Drawing Sheets

PORTABLE SPECTROPHOTOMETRIC INSTRUMENT HAVING VIAL HOLDER AND LIGHT INTEGRATOR

CROSS REFERENCE TO COPENDING APPLICATION

This is a continuation of my U.S. Application 412,453 entitled "Portable Colorimetric, Instrument" which was filed on Sept. 26, 1989.

TECHNICAL FIELD

This invention relates to the art of analytical instruments. In particular, the invention is a portable instrument capable of performing accurate spectrophotometric measurements in the field.

BACKGROUND ART

It is known to measure the concentration of a substance by addition of a reagent which reacts with the substance to produce a colored compound, the optical density of which is a function of the concentration of the substance.

The use of a narrow ampoule for receiving a sample for colorimetric measurements is also know and is described in U.S. Pat. No. 3,634,038.

Spectrometric measurements are generally made with a technique which provides a reference signal. The use of light having two wavelengths wherein one of the wavelengths serves as a reference is shown, for example, in U.S. Pat. Nos. 3,887,281 (Kurita) and 4,297,579 (Spaeth). These references teach comparison of the reference and sample signals by electronically producing the difference of the logarithms of the signals.

SUMMARY OF THE INVENTION

In accordance with the invention, a portable instrument is provided which is capable of accurate colorimetric field measurements of substances such as dissolved oxygen. The instrument includes a body which has a receptacle for an elongate cylindrical vial which is self-filling. In the preferred embodiment, a door is pivotally attached to the body and has a holder for receiving the vial. When the door is opened, preferably by pivoting it 45° with respect to the body, the vial may be inserted into the holder. When the door is closed, the vial is automatically placed in the proper position in the receptacle.

The body encloses an optical system for illumination of the vial. The optical system comprises two sources of light, a first of the sources producing light which is absorbed by the sample and the second of the sources producing light which is absorbed only to a small degree by the sample. The light from the first source is the measuring beam while the light from the second source is a reference beam. These beams are produced by alternatingly powered light emitting diodes (LED).

When the vial is in the receptacle, it is aligned with an optical path of an illuminating beam produced by the first and second sources of light. Preferably, the optical path is aligned with the longitudinal axis of the vial so that the path length of the beam in the sample is as long as possible. In a preferred embodiment, the light path within the fluid sample is about 70mm. The light enters through the base of the vial and exits from the top of the vial. A light integrator surrounds the top of the vial and directs the emerging light to a diffuser and a detector. The integrator preferably comprises two semi-cylindrical parts. One of the parts is in the body of the instrument, and the other is in the door so that the two match to form a complete cylinder when the door is closed.

The signals from the light detector are directed to an amplifier and to a microprocessor which determines the difference between the logarithms of the two signals along with other signal processing which will be described in more detail below.

An object of this invention is to provide a highly accurate portable instrument capable of field measurements.

Another object of this invention is to provide a portable instrument into which a self filling vial may easily be inserted for performing colorimetric measurements in the field.

DETAILED DESCRIPTION OF THE PREFERRED EMBODIMENT

Figure 1:
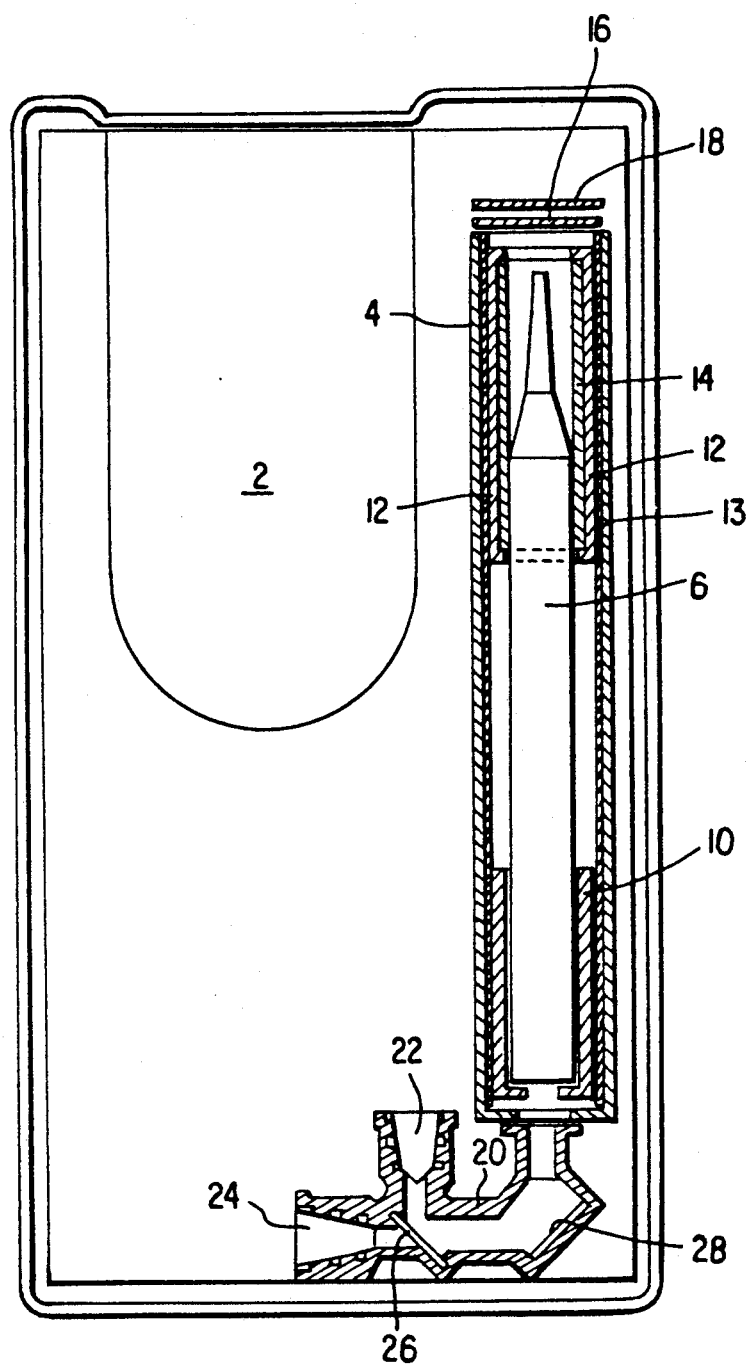
FIG. 1 is a plan view of an instrument in accordance with the invention.
Figure 2:
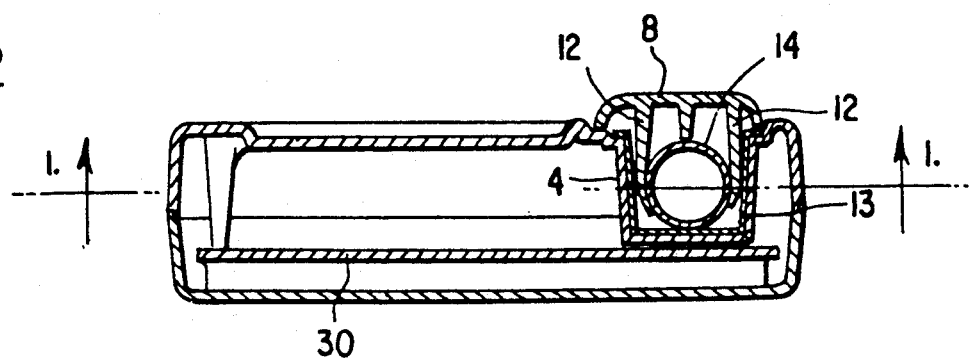
FIG. 2 is a transverse cross section of the instrument shown in FIG. 1.

With reference to FIGS. 1 and 2, a preferred embodiment of the instrument in accordance with the invention comprises a body 2 having a receptacle 4 for receiving a vial 6. The vial is preferably that shown in U.S. Pat. No. 3,634,038 which is specifically designed for colorimetric measurements.

The receptacle is covered by a door which is pivotally mounted to the body 2 at the bottom of the door. The door has a cylindrical holder 10 which receives the bottom of the vial 6. This holder has an aperture for allowing the illuminating beam to pass to the vial as will be described in more detail with reference to FIG. 3. The upper end of the vial is received by fingers 12 which are flexible to releasably receive the vial. The fingers and the holder are spaced to provide a gap which allows light emanating from the vial in unwanted directions to escape.

A tray 13 extends the length of the vial and lines the receptacle to prevent the spillage of liquid from the vial into the body.

An integrator 14 surrounds the upper end of the vial to direct the light which has passed through the vial to a diffuser 16 and then to a detector 18. The diffuser and detector are mounted in the body 2 at locations such that the top of the vial and the integrator are aligned with them when the door is closed. The integrator is preferably cylindrical and may be a complete cylinder held in the door and into which the vial is slid or may comprise two semi-cylinders, one of which is in the door and the other of which is in the body such that a complete cylinder is formed when the door is closed.

The lower part of the body includes a molded structure 20 which supports a red LED 22, a green LED 24, a beam combining mirror 26, and a reflective mirror 28. The red LED 22 preferably emits at 660nm and the green LED emits at 555nm. The beam combiner 26 is transmissive to green light and reflective to red light to combine the light from the LED's and direct it to the mirror 28 which directs the light through an aperture in the bottom of the holder and then to the bottom of the vial. The molded structure is designed to provide baffles which absorb stray light and which provide apertures for the transmission of collimated light from the LED's to the bottom of the vial 6.

A circuit board 30 is mounted in the body below the receptacle for supporting the electronic circuitry which will be described with reference to FIG. 5.

Figure 3:
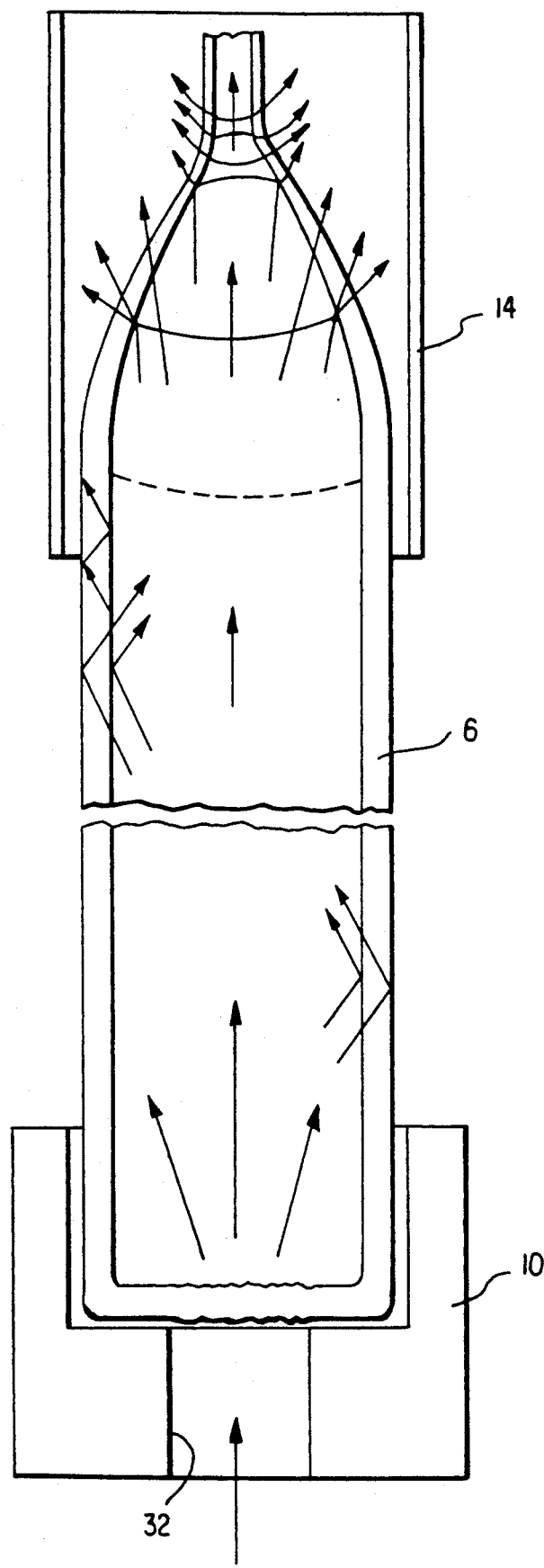
FIG. 3 is a longitudinal cross section of the sample vial and receptacle of the instrument shown in FIG. 1.

Referring to FIG. 3, light from the mirror 28 is directed through an aperture 32 in holder 10 and illuminates the bottom of vial 6. The aperture is optically distant from the LED's to provide collimated rays of light for illumination of the vial. The diameter of the aperture is less than that of the vial so that the light passes through the bottom and into the sample with very little being transmitted into the side walls of the vial. This reduces the amount of light which is lost and increases the accuracy of the measurement. As shown in FIG. 3, some of the light passes directly through the vial and out the other end to be detected by a silicon detector 18, but a large part of the light does not follow such a direct path. The bottom of the vial necessarily scatters the light somewhat because of the sealing of the bottom during manufacture. This light then impinges on the walls of the vial at a range of angles. Those which impinge at small angles of incidence will pass through the vial and are allowed to exit the receptacle through the gap provided between the integrator 14 and the holder 10. This gap is 50-60% 60% of the length of the vial. In addition, other surfaces which would have significant reflections are spaced from the vial. Those rays which are at larger angles, particularly those above the critical angle, are trapped within the vial. These rays can be trapped by reflections at the liquid-glass interface or the glass-air interface. The light which is trapped in the wall of the vial is unwanted light, the effects of which can be removed during standardization.

The liquid at the top of the vial forms one or more menisci which also disperse the light away from the axis of the vial. This light passes to the outside of the vial and is collected by the integrator 14 which surrounds the top of the vial. The integrator is provided with a diffuse reflective surface such that chromatic dispersion which occurs at the various interfaces is eliminated and does not affect the location of impingement of the light on the detector.

Figure 4:
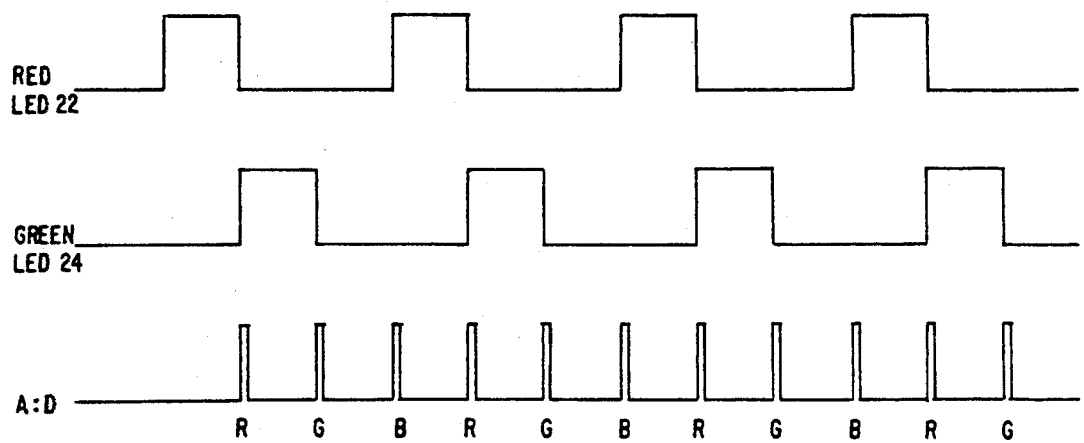
FIG. 4 is a timing diagram illustrating pulses detected from the integrator.
Figure 5:
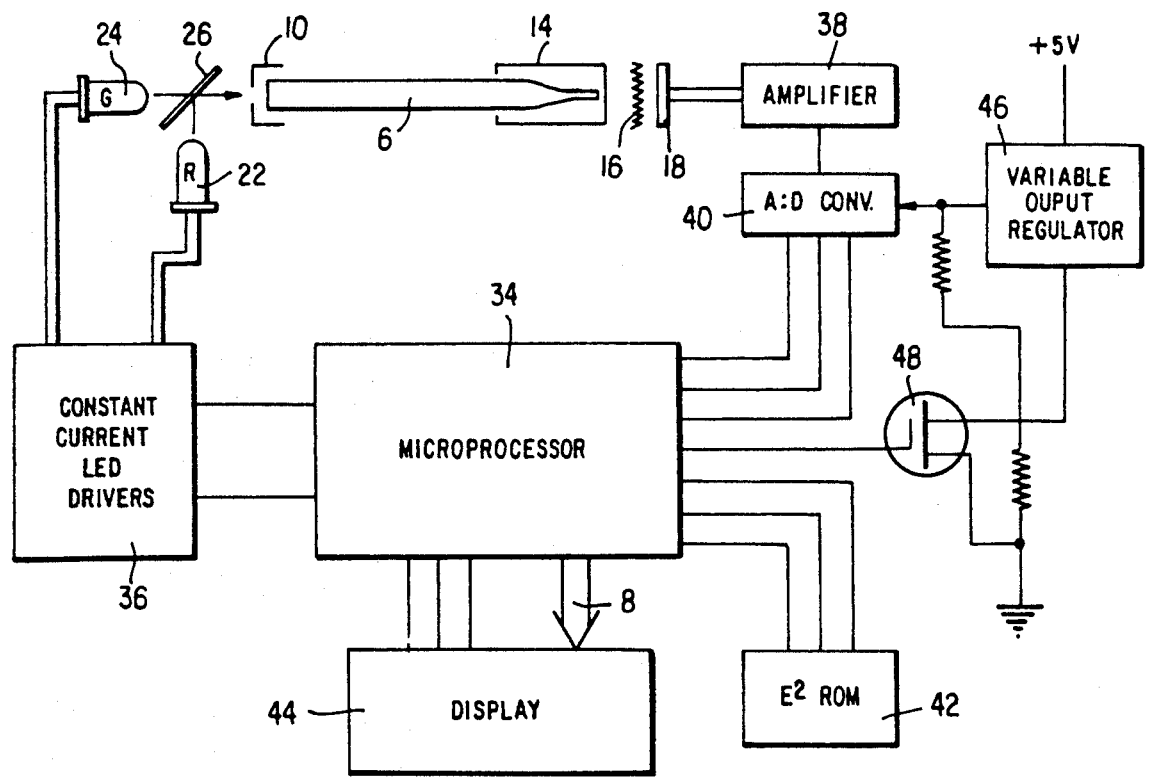
FIG. 5 is a block diagram of the preferred circuit of the instrument shown in FIG. 1.

FIG. 5 is a block diagram of a preferred circuit, and FIG. 4 is a diagram illustrating the timing of the light pulses from the LED's and the sampling of the signals from the detector. A microprocessor 34 controls constant current LED drivers 36 to cause the LED 22 to produce light as shown by the top line in FIG. 4. The LED 24 is driven to provide a light beam as shown by the middle line in FIG. 4. The current is preferably such that the two LED's produce equal outputs on the detector with no sample present.

The LED's are driven to produce pulses at a rate of about 20Hz and the pulses are about 0.05 sec. in length. The microprocessor samples the signal from the detector at the tail end of the pulse to give the input amplifier time to stabilize. In other words, a sample is taken just before the red LED is turned off and just before the green LED is turned off. A background sample is taken after the red and green LED's have been turned off and just before the red LED is reactivated. The sampling is illustrated by the lower line of FIG. 4. Averages of four samples of each of the red, green, and background signals are used in the processing.

The signal from the detector 18 is fed to a transimpedence amplifier 38 and then to an analog to digital converter 40. The A:D converter converts the voltage from the amplifier 38 to an 8-bit serial stream which is received by the microprocessor 34. An $E^2PROM$ 42 is provided for storing the calibration values of the instrument. Each time the instrument is calibrated or zeroed, the values in the $E^2PROM$ are updated.

The instrument has four modes which are controlled through a switch which supplies signals to the microprocessor 34. When a "select" switch is pressed, power is supplied to the microprocessor which provides a signal to the power supply to keep it turned on and to allow the same switch to select one of the modes. The particular mode selected is shown on a display 44 so that activation of a "run" switch causes that operation to be performed. In the ready mode, the microprocessor may make a measurement. In the original calibration mode, the instrument recalls the factory set calibration data from the $E^2PROM$. When in the zero mode, the instrument makes a measurement of a vial filled with distilled water. In this zeroing step, the microprocessor calculates the difference between the logarithms of the red and green signal samples. The microprocessor remembers this zero log difference value and subtracts it from the log values calculated during a measurement of a test sample.

The measurement made by the instrument is to determine the difference between the logarithms of the measured green and red signals. Because the intensities of the green and red light sources can be made equal mathematically (by the zeroing step), the difference between the logarithms is proportional to the concentration of the substance to be measured in the sample. The proportionality constant is measured in the calibration step and is retained in the $E^2PROM$ memory. This value is multiplied in the processor by the difference of the logarithms of the red and green samples corrected by the zero factor.

Standardization consists of the initial zero calculation and proportionality factor calculation and placement of these values in the $E^2PROM$ location used to store the original calibration data. The instrument is standardized at the factory with these factors which may be recalled through the "original calibration" function.

Because the turbidity of the sample affects the range of the values produced by the detector, a correction has been supplied for providing a full range output for these reduced values. The A:D converter 40 is supplied with a reference voltage produced by a variable output regulator 46 which sets the reference voltage of the converter at either 1.25v or 2.5v. The microprocessor detects when the dynamic range is low and supplies a signal to the gate of MOSFET 48. The drain of the MOSFET is connected to the adjust terminal of the variable output regulator and the intersection of two resistors connected in series between the output of the variable output regulator and ground. These resistors are 620 ohms and 1K ohms respectively. When the gate of the MOSFET is energized, the voltage at the intersection of the resistors is pulled to ground which causes the variable output regulator to produce an internally set voltage of 1.25v above ground. When the gate is not energized, the voltage at the intersection of the resistors rises to about 1.25v which means the variable output regulator provides an output voltage of 2.5v. It will be appreciated that this effectively provides two ranges for the instrument.

Preferably, the range of the instrument is set automatically. If the signal strengths are low, the microprocessor will order another conversion at twice the resolution by operation of the MOSFET 48 to control the reference voltage of the A:D converter.

In operation, the processor receives the data from the A:D converter and subtracts the average background from the average red and the average green values. It then determines the logarithms of the red and green signals and determines the differences between these logarithms. The value of the difference between the logarithms determined during the zeroing process, which is a zeroing measurement with distilled water, is then subtracted from the measured values of the sample to correct for any imbalance between the red and green values. This value is then multiplied by the value of the calibration constant retained in the E$^2$PROM obtained by the original calibration step. The result is converted to a BCD number, and the display is composed, which indicates the concentration.

While the above description is based on the measurement of a sample for a single substance, it will be appreciated that measurements for a plurality of substances could be made by providing a selection for the original calibration values for other substances. In addition, while an instrument having two light sources has been shown, it is contemplated that a plurality of sources could be provided and controlled to operate in pairs as described above.

Modifications within the scope of the appended claims will be apparent to those of skill in the art.

I claim:

1. Apparatus for optical analysis of a sample comprising a body having receptacle means for receiving a sample vial, illumination means for illuminating said sample vial through a base of said vial, and detector means for detecting light which has passed through said sample vial, wherein said receptacle means comprises holder means for engaging said base of said vial and integrator means spaced from said holder for surrounding the upper part of said vial and integrating light emerging from said vial.

2. Apparatus according to claim 1 wherein said illumination means comprises a source of light and a mirror for directing said light toward said holder.

3. Apparatus according to claim 1 wherein a body of said vial is cylindrical, and said mirror directs light in the direction of a longitudinal axis of said body.

4. Apparatus according to claim 3 wherein said source of light comprises a first source of light of a first wavelength and a second source of light of a second wavelength, wherein light of said first wavelength provides a reference illumination.

5. Apparatus according to claim 4 further comprising means for determining the difference between the logarithms of the signals from said detector for each of said wavelengths.

6. Apparatus according to claim 1 wherein said body has a recess and said receptacle means further comprises a door for covering said recess and means for pivotally attaching said door to said body, wherein said holder is attached to said door.

7. Apparatus according to claim 6 wherein said means for pivotally attaching said door to said body is at one end of said door.

8. Apparatus for optical analysis of a sample comprising a body having receptacle means for receiving a sample vial, illumination means for illuminating said sample vial through a base of said vial, and detector means for detecting light which has passed through said sample vial, wherein said receptacle means comprises holder means for engaging said base of said vial and integrator means spaced from said holder for integrating light emerging from said vial and further comprising analog to digital converter means for supplying a digital processor with digital signals derived from said detector, means for changing the sensitivity of the measurement comprising means for supplying a reference voltage to said analog to digital converter means, and means for adjusting said reference voltage.

9. Apparatus according to claim 8 wherein said means for supplying a reference voltage comprises a variable output regulator.

* * * * *